United States Patent [19]

Wright

[11] Patent Number: 5,489,215
[45] Date of Patent: Feb. 6, 1996

[54] MEDICAL ELECTRODE

[75] Inventor: Richard A. Wright, Westminster, Mass.

[73] Assignee: Micron Medical Products, Inc., Fitchburg, Mass.

[21] Appl. No.: 319,233

[22] Filed: Oct. 6, 1994

Related U.S. Application Data

[62] Division of Ser. No. 113,420, Aug. 27, 1993.

[51] Int. Cl.⁶ ............................. H01R 4/58; A61B 5/04
[52] U.S. Cl. ............................................. 439/86; 128/641
[58] Field of Search ...................... 439/86, 909; 128/641

[56] References Cited

U.S. PATENT DOCUMENTS

| | | | |
|---|---|---|---|
| 3,964,469 | 6/1976 | Manley | 128/2.1 E |
| 3,976,055 | 8/1976 | Monter et al. | 128/2.06 E |
| 4,016,869 | 4/1977 | Reichenberger | 128/2.1 E |
| 4,090,760 | 5/1978 | Furey | 339/61 R |
| 4,094,571 | 6/1978 | Benjamin | 339/91 R |
| 4,126,126 | 11/1978 | Bare et al. | 128/2.06 E |
| 4,165,141 | 8/1979 | Williams et al. | 339/75 R |
| 4,166,456 | 9/1979 | Wilson | 128/640 |
| 4,197,851 | 4/1980 | Fellus | 128/422 |
| 4,282,878 | 8/1981 | Novello | 128/641 |
| 4,304,453 | 12/1981 | Grunwald | 339/75 R |
| 4,317,278 | 3/1982 | Carmon et al. | 29/878 |
| 4,365,634 | 12/1982 | Bare et al. | 128/640 |
| 4,367,755 | 1/1983 | Bailey | 128/798 |
| 4,370,984 | 2/1983 | Cartmell | 128/640 |
| 4,401,356 | 8/1983 | Bare | 339/258 R |
| 4,458,696 | 7/1984 | Larimore | 128/798 |
| 4,539,996 | 9/1985 | Engel | 128/640 |
| 4,543,958 | 10/1985 | Cartmell | 128/640 |
| 4,556,051 | 12/1985 | Maurer | 128/1.5 |
| 4,570,637 | 2/1986 | Gomes et al. | 128/639 |
| 4,681,497 | 7/1987 | Berecz | 439/86 X |
| 4,685,467 | 8/1987 | Cartmell et al. | 128/641 |
| 4,742,828 | 5/1988 | Sundstrom | 128/641 |
| 4,915,656 | 4/1990 | Alferness | 439/909 X |
| 5,199,432 | 4/1993 | Quedens et al. | 439/909 X |
| 5,265,579 | 11/1993 | Ferrari | 128/640 |
| 5,355,883 | 10/1994 | Ascher | 439/909 X |

FOREIGN PATENT DOCUMENTS

| | | |
|---|---|---|
| 1144606 | 4/1983 | Canada. |
| 0210020 | 1/1987 | European Pat. Off. |
| 0510786 | 10/1992 | European Pat. Off. |
| 9316259 | 2/1994 | Germany. |
| 2203344 | 10/1988 | United Kingdom. |
| 91/11834 | 8/1991 | WIPO ................................. 128/641 |

*Primary Examiner*—Larry I. Schwartz
*Assistant Examiner*—Daniel Wittels
*Attorney, Agent, or Firm*—Bromberg & Sunstein

[57] ABSTRACT

A medical electrode having a resilient terminal press fit onto an eyelet. The eyelet is plastic and has a conductive coating thereon. The terminal is made of a resilient nonmetallic composition, such as a polypropylene blend loaded with carbon fiber. An electrolyte composition is spread upon the bottom of the eyelet for making electrical contact with the skin of a patient. The eyelet, the terminal and the electrolyte composition are preferably all at least translucent to x-rays.

4 Claims, 1 Drawing Sheet

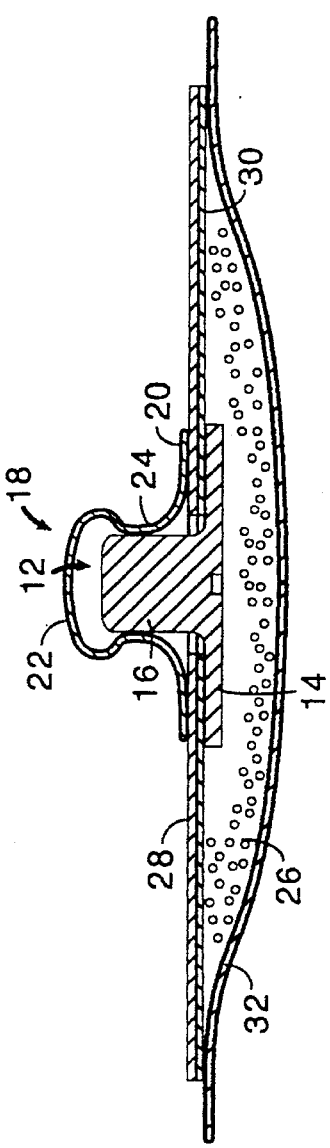
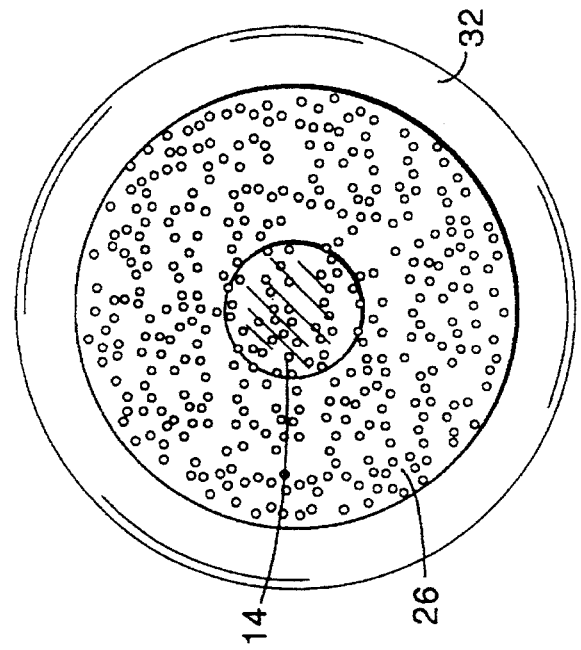
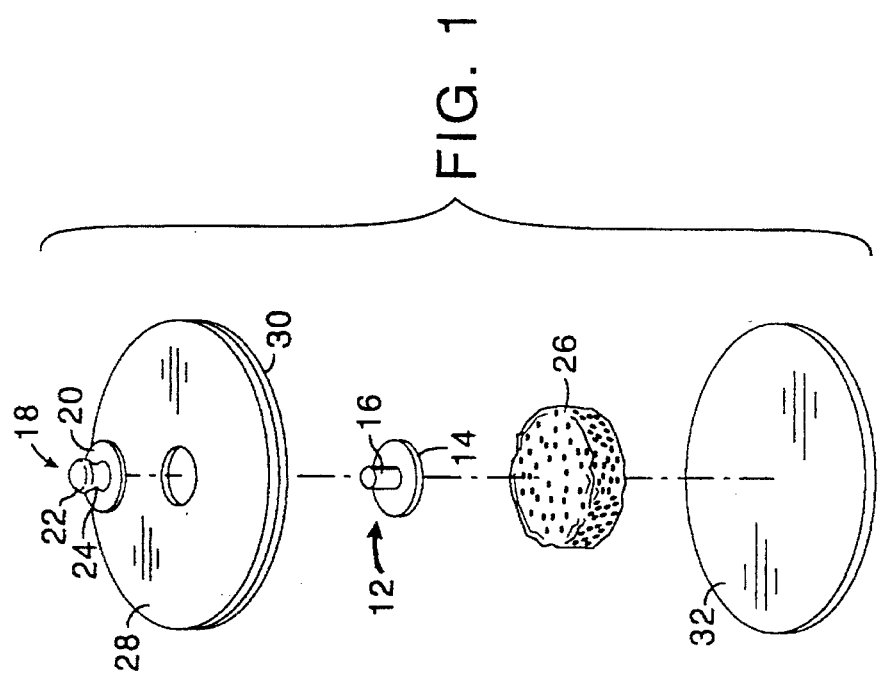

MEDICAL ELECTRODE

This is a divisional of application Ser. No. 08/113,420 filed on Aug. 27, 1993.

BACKGROUND OF THE INVENTION

The present invention is directed to a medical electrode for temporary adhesive placement on a patient. More particularly, this invention relates to a two piece conductor adapted for interconnection between an electrolyte and suitable signal processing or monitoring equipment.

U.S. Pat. No. 3,964,469 describes a disposable electrode having a two piece conductor in contact with a gel pad. The part of the conductor in contact with the gel pad is a silver plated plastic snap fastener eyelet. The second part of the conductor is a conventional metal snap fastener stud.

U.S. Pat. No. 3,976,055 discloses an electrode with a conductor that can be molded in one piece. The conductor formed in one piece is made of a plastic rendered conductive by including carbon and a modest percentage of metal particles. The patent further discloses an alternate embodiment in which a second part of the conductor includes a conventional metal snap fastener that is press fit onto the first conductor. The two piece conductor disclosed in both patents recited herein will interfere with an x-ray.

SUMMARY OF THE INVENTION

In accordance with the present invention, a new electrode terminal replaces the metal snap of the prior art. The electrode terminal of the invention is a conductor made from a conductive resilient nonmetallic composition. The composition may be a resilient plastic composition loaded with carbon fiber. The other conductive part into which the terminal is press fit is a metallic coated plastic eyelet. The resilient terminal is advantageously less likely to shear off portions of the metallic coating on the eyelet when press fit thereon as compared with a rigid terminal such as one made of metal or ABS.

The metallic coating on the eyelet is made from either silver or silver salt. The thickness of the coating is sufficient to provide the necessary conductivity, but is thin enough to substantially avoid interfering with x-rays. The entire electrode of the present invention is translucent to x-rays. The design of a two-piece x-ray translucent electrode is able to take advantage of the abundant manufacturing capacity of existing two-piece electrode assembly machines.

Other objects and advantages of the invention will become apparent during the following description of the presently preferred embodiment of the invention taken in conjunction with the drawings.

BRIEF DESCRIPTION OF THE DRAWINGS

FIG. 1 is an exploded view of a medical electrode of the present invention.

FIG. 2 is a side cross section view of the medical electrode of FIG. 1.

FIG. 3 is a bottom plan view of the medical electrode of FIG. 1.

DESCRIPTION OF THE PREFERRED EMBODIMENT

Referring now to the drawings, the present invention shall be described in the context of a conventional electrode arrangement as shown in FIGS. 1, 2 and 3. The electrode arrangement discussed herein has been selected for illustration purposes only and is not meant to limit the scope of the invention to use therein. Rather, the terminal and two part conductor of the invention may be used in any of a wide variety of electrode arrangements. Machinery for producing medical electrodes with two part conductors is commonly available in the industry.

A first conductor is formed by an eyelet 12. The eyelet 12 is formed of a disc 14 and a post 16 sticking up from the disc 14. The bottom surface of the disc 14 provides a surface area for mounting proximate to the skin of a patient. The eyelet 12 is generally made from plastic. The plastic may be mixed with a conductive material. The eyelet is formed in a mold. In the presently preferred embodiment, the eyelet is made from acrylic butylstyrene (ABS) loaded with glass of about 20% by weight. A conductive layer is coated about the plastic eyelet 12. Preferably, the conductive coating is made from silver or a silver salt such as silver chloride. The conductivity of the eyelet must satisfy AAMI standards in order to prevent loss of ECG readings from the patient during and after defibrillation. In accordance with the present invention, the thickness of the conductive coating is preferably thin enough to be at least x-ray translucent (if not transparent) and yet thick enough to provide sufficient conductivity to meet the safety requirement for defibrillation. The thickness of the metallic coating should be within the range of from 0.02 to 0.10 mils depending largely upon the conductivity of the eyelet material. In accordance with the presently preferred embodiment, the conductive coating is 0.065 mils in thickness. The presently preferred method for coating the plastic eyelet with the silver or silver chloride is through the use of electroless plating. Conventional electroplating may be used instead of or in addition to electroless plating to get the desired coating thickness. Another alternative coating method is to spray a silver-silver chloride ink on the plastic eyelet.

A second conductor is used as the terminal 18 of the electrode. The terminal 18 is shaped as a hollow stud that can be press fit onto the post 16 of the plastic eyelet 12. The hollow stud of terminal 18 sits atop an annular disc 20 having a hole therein. The hollow stud is preferably formed integral with the annular disc in a mold. The hollow stud includes a top crown portion 22 and a bottom waist portion 24. The bottom waist portion 24 extends up from the annular disc 20 and encircles the hole in the disc. The top crown portion 22 is preferably wider in circumference than the base waist portion 24 of the stud. The top crown 22 portion may thus be grabbed onto by an electrical apparatus for making a sufficiently secure electrical connection. The hollow cavity within the stud has a sufficiently small inner diameter to snugly fit about the post 16 of the plastic eyelet 12.

The terminal 18 of the present invention is made from a conductive resilient composition. The terminal 18 is resilient so that when it is press fit, i.e., snapped onto, the plastic eyelet, the metallic coating on the plastic eyelet remains substantially intact. Another advantage of using a resilient material is so that when it is press fit over the post 16, the terminal does not crack.

In addition, the terminal 18 of the invention is nonmetallic so that it is at least translucent to x-rays. The presently preferred composition for the terminal 18 is a plastic composition loaded with a conductive material, such as carbon fiber. In particular, the presently preferred plastic is a polypropylene and carbon 50—50 blend loaded with carbon fibers to about 20% by weight. It has been found that the polypropylene blend loaded with carbon fibers provides sufficient conductivity and is sufficiently resilient to form a tight fit over the post 16 without cracking when it is press fit thereover.

In order to provide a conductive path to the skin of a patient, an electrolyte composition 26 is applied about the bottom surface of the eyelet 12. The electrolyte composition 26 is generally a gel or jelly, either by itself or soaked throughout a pad of cellular material. Suitable conductive gels for this purpose are well known in the art. Commonly used gel materials for providing the conductive path from the bottom surface of the eyelet to the skin include hydrogel, adhesive gel and liquid gel. Any of these commonly used gels or equivalents may be combined with the two part conductor of the present invention to form an electrode.

The terminal 18 should fit tightly over the post 16 on the eyelet. Metallic terminals in conventional two-part electrodes have been known to fail to meet the defribillation recovery standards when gel seeps between the terminal and the eyelet. This is due to a battery effect. The resilient nonmetallic terminal is less apt to fail due TO such gel seepage.

In order to keep the electrolyte 26 beneath the electrode, a nonporous separator sheet 28 is mounted between the disc of the terminal 18 and the disc of the eyelet. The nonporous sheet 28 may also serve to provide a location on which a manufacturer can indicate its name for the product.

The composition of the electrode of the invention can also be defined electrically. The metallic coating on the eyelet 12 and the conductive material in the terminal 18 provides sufficient conductivity so that the completed electrode has an AC impedance at 10 Hz of less than 200 ohms before and after performing a defribillation. The conductivity can be adjusted by changing the thickness of the metallic coating on the eyelet 12 and/or the quantity of conductive material in the terminal 18.

In order to keep the electrode on the skin of a patient, an adhesive is generally included on the electrode. The electrolyte 26 may itself be an adhesive gel. While this may be sufficient, typically, an adhesive layer 30 is a part of the electrode. A common arrangement is to provide an adhesive layer 30 on the underside of the nonporous sheet 28. Before the electrode is put into use, a removable backing sheet 32 covers the adhesive layer 30. In the simple electrode arrangement shown in the drawings, the backing sheet 32 is made of a nonporous transparent plastic so as to prevent the electrolyte composition from leaking through.

Alternative electrode arrangements may include a plastic foam ring. In this case, the adhesive layer may be provided on the bottom side of the foam ring. The top side of the foam ring is firmly adhered to the nonporous separator sheet. The foam makes a ring around the electrolyte composition.

To use the electrode of the present invention, the removable backing sheet 32 is peeled off the bottom of the electrode revealing the electrolyte composition. The electrolyte composition 20 remains stuck to the bottom surface of the disc on the eyelet 12. The electrode can then be pressed against the skin. The adhesive in the electrolyte composition or the adhesive layer 30 serves to hold the electrode to the skin. The electrolyte 20 provides electrical conductivity between the skin and the two part conductor. All pieces of the electrode of the present invention are advantageously at least translucent to x-rays so that x-ray photos of the patient can be made without the removal of the electrodes. The electrode of the present invention is advantageously made with a two part conductor so that the assembly machines commonly available in the industry may be used in the assembly of the x-ray translucent electrode.

Of course, it should be understood that various changes and modifications to the preferred embodiment described above will be apparent to those skilled in the art. For example, there are many ways to arrange an electrode with a two part conductor mounted therein. The electrode may include a foam ring, a plastic reservoir cover for the electrolyte and paper backing sheets. These and other changes can be made without departing from the spirit and scope of the invention and without diminishing its attendant advantages. It is therefore intended that such changes and modifications be covered by the following claims.

What is claimed is:

1. A terminal for use on a medical electrode comprising:

an annular disc having a hole therein;

a hollow stud having a crown portion and a base portion, the crown portion being larger in circumference than the base portion and the base portion extending up from said disc and encircling the hole; and said disc and said hollow stud being integrally formed of a resilient polyproplylene composition loaded with a conductive material.

2. The terminal of claim 1 wherein the conductive material comprises carbon fiber.

3. The terminal of claim 2 wherein the resilient polypropylene composition is loaded with at least about 20% by weight of carbon fiber.

4. The terminal of claim 1 wherein the resilient polypropylene composition is at least translucent to x-rays.

\* \* \* \* \*